US00PP35481P2

(12) United States Plant Patent
Bloom

(10) Patent No.: US PP35,481 P2
(45) Date of Patent: Nov. 14, 2023

(54) ***CAMPANULA* PLANT NAMED 'PURPLE FOUNTAIN'**

(50) Latin Name: *Campanula poscharskyana*
Varietal Denomination: Purple Fountain

(71) Applicant: Adrian Bloom, Bressingham (GB)

(72) Inventor: Adrian Bloom, Bressingham (GB)

( * ) Notice: Subject to any disclaimer, the term of this patent is extended or adjusted under 35 U.S.C. 154(b) by 0 days.

(21) Appl. No.: 18/091,627

(22) Filed: Dec. 30, 2022

(51) Int. Cl.
*A01H 5/02* (2018.01)
*A01H 6/26* (2018.01)

(52) U.S. Cl.
USPC ..... Plt./414
CPC ..... *A01H 6/264* (2018.05)

(58) Field of Classification Search
USPC ..... Plt./414
CPC ..... A01H 6/264; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Campanula* plant named 'Purple Fountain' is disclosed, characterized by low-growing plant habits, purple flowers with white throats, and green foliage tinged with purple. The new variety is a *Campanula*, typically produced as an outdoor ornamental plant.

2 Drawing Sheets

Figure 1:
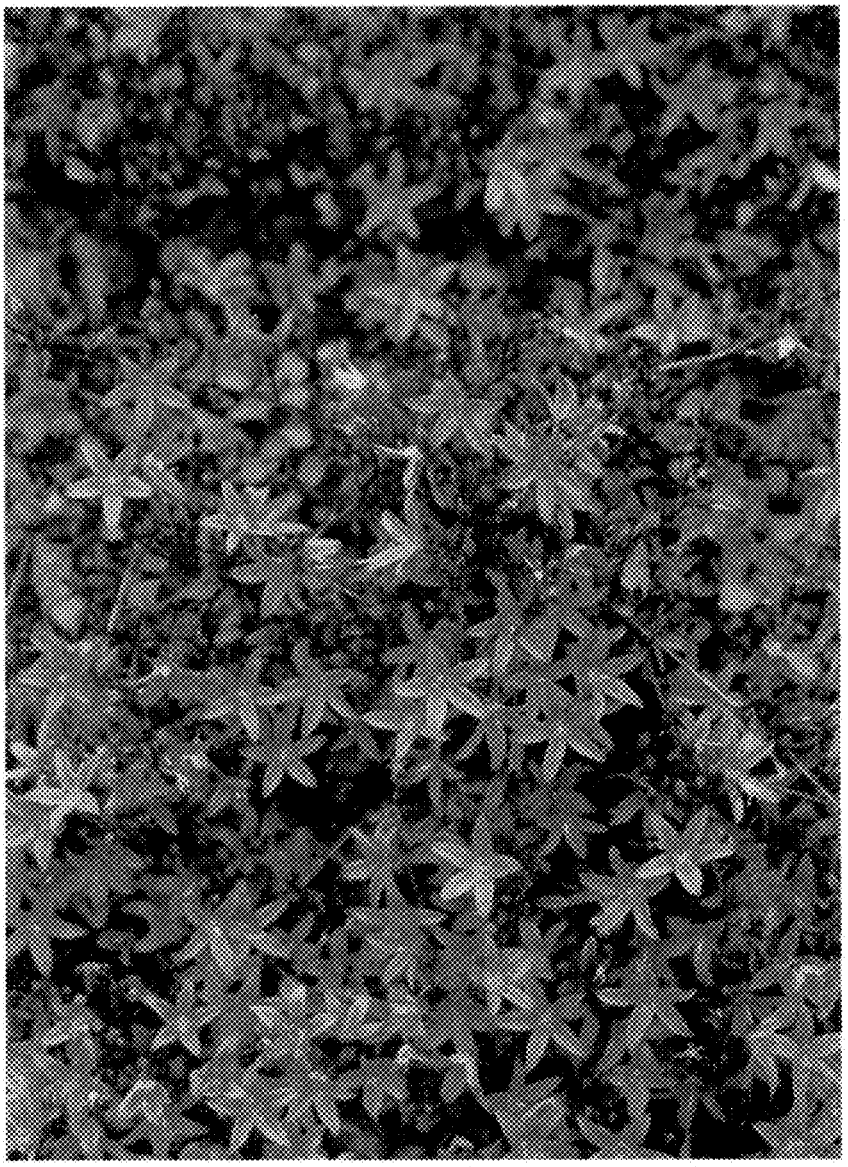

Latin name of the genus and species: *Campanula poscharskyana.*
Variety denomination: 'PURPLE FOUNTAIN'.

BACKGROUND OF THE INVENTION

The new cultivar is a product of chance discovery by the inventor at a research garden. The new variety was found and selected as an individual seedling plant emerging in a population of unpatented, unnamed *Campanula poscharskyana* varieties at a research garden in Norfolk, United Kingdom in 2007.

The exact parentage cannot be determined.

Asexual reproduction of the new cultivar 'Purple Fountain' was first performed during 2010 in Norfolk, United Kingdom, by basal cuttings. Through subsequent propagation, multiple additional generations have been reproduced, having shown that the unique features of this cultivar are stable and reproduced true to type.

SUMMARY OF THE INVENTION

The cultivar 'Purple Fountain' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Purple Fountain'. These characteristics in combination distinguish 'Purple Fountain' as a new and distinct *Campanula* cultivar:

1. Purple-tinged leaves early in the year.
2. 20 cm stems.
3. Low-growing.
4. Purple flowers with white throats.

PARENT COMPARISON

The new variety 'Purple Fountain' differs from the population of unpatented, unnamed *Campanula poscharskyana* varieties from which it originated in the following:

1. 'Purple Fountain' is shorter and more prostrate than the population it was selected from.
2. 'Purple Fountain' consistently produces purple-tinged leaves; the population it was selected from had inconsistent, few or no purple foliage
3. 'Purple Fountain' was the only varieties with purple flowers having a white center in the population it was selected from.

COMMERCIAL COMPARISON

Plants of the new cultivar *Campanula* 'Purple Fountain' can be compared to the commercial variety *Campanula poscharskyana* 'Camgood', U.S. Plant Pat. No. 13,161. Plants of 'Purple Fountain' are similar to plants of 'Camgood' in most horticultural characteristics, however, plants of 'Purple Fountain' differ in the following:

1. Leaves of the new variety are green tinged with purple, while leaves of this comparator are green.
2. Flowers of the new variety are a distinctly darker violet color than flowers of this comparator.

Plants of the new cultivar *Campanula* 'Purple Fountain' can be compared to the commercial variety *Campanula poscharskyana* 'Lisduggan', unpatented. Plants of 'Purple Fountain' are similar to plants of 'Lisduggan' in most horticultural characteristics, however, plants of 'Purple Fountain' differ in the following:

1. Leaves of the new variety are green tinged with purple, while leaves of this comparator are purple.
2. Flowers of the new variety are Violet with white throats, while flowers of this comparator are entirely colored very light lavender.

BRIEF DESCRIPTION OF THE PHOTOGRAPHS

The accompanying photograph in FIG. 1 illustrates in full color a close up of flowers of 'Purple Fountain'.

Figure 2:
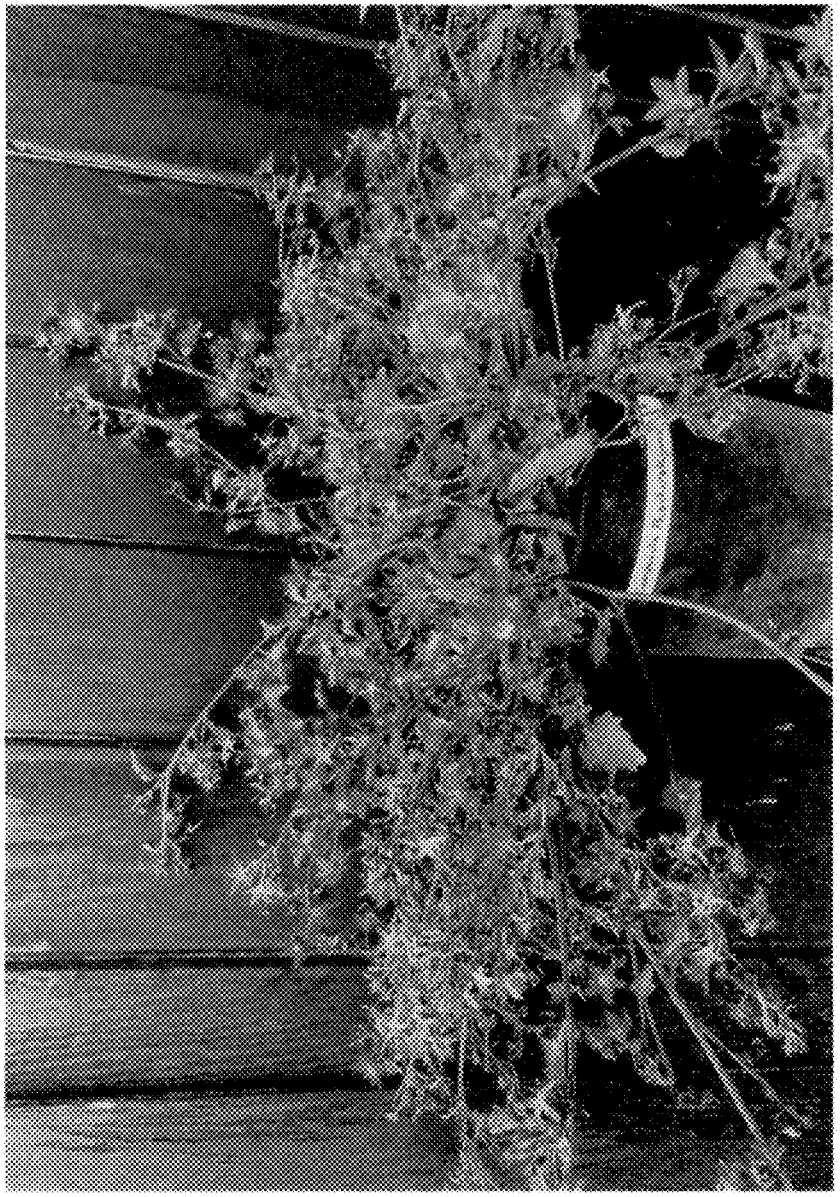

FIG. 2. Illustrates a typical plant of 'Purple Fountain' grown outdoors in Dayton, Oreg. This plant is approximately 9 months old, grown in a 1-gallon container.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'Purple Fountain' plants grown outdoors in Dayton, Oreg. The plants were about 5 months old. Temperatures ranged from 4° C. to 12° C. at night to 15° C. to 30° C. during the day. No artificial light, photoperiodic treatments were given to the plants. Measurements and numerical values represent averages of typical plant types.

Botanical classification: *Campanula poscharskyana* 'Purple Fountain'.

PROPAGATION

Time to initiate roots: About 10 days at 20° C.

Time to produce a rooted cutting: About 30 days at 20° C.

Root description: Dense and fibrous, freely branching. About 2 to 4 mm in diameter. Colored near RHS Greyed-Green 196D and 197D.

PLANT

Age of plant described: Approximately 5 months.

Pot size of plant described: 1-gallon.

Growth habit: Low, prostrate flowering perennial.

Height: 15 to 18 cm.

Plant spread: 55 to 65 cm.

Growth rate: Moderate.

Stem characteristics: Well branched, basal and lateral branching.

- *Length*.—22 to 32 cm.
- *Diameter*.—3 to 4 mm.
- *Quantity of stems per plant*.—About 30 to 50 basally emerging stems, lateral branching rare.
- *Color*.—Near RHS Yellow-Green 146A with a very strong overall flush near Greyed-Purple N187B.
- *Texture*.—Glabrous, ridged.

Internode length: 2 to 3.5 cm.

FOLIAGE

Leaf:

- *Arrangement*.—Basally emerging.
- *Quantity*.—Approximately 60 to 70 per plant.
- *Average length*.—3 cm to 4.5 cm.
- *Average width*.—2 to 3 cm.
- *Shape of blade*.—Cordate.
- *Apex*.—Acute.
- *Base*.—Cordate.
- *Margin*.—Dentate to double dentate.
- *Texture of top surface*.—Glabrous.
- *Texture of bottom surface*.—Glabrous.
- *Color*.—Young foliage, upper side: Near RHS Green 137A, flushed 143A. Young foliage, under side: Near RHS Green 138C. Mature foliage, upper side: Near RHS Green 137A, with a blotchy flush near Greyed-Purple N186C. Mature foliage, under side: Near RHS Green 138C blotched along margin near Greyed-Purple N186C.
- *Venation*.—Type: Pinnate. Color, upper side: Near RHS Green 137A. Color, under side: Near RHS Green 138C.

Petiole:

- *Length*.—Average 3 cm to 5.2 cm.
- *Diameter*.—Average 2 to 3 mm.
- *Color*.—Near RHS Green 138C.
- *Texture*.—Glabrous.

FLOWER

Natural flowering season: Spring and summer.

Inflorescence:

- *Type and habit*.—Panicle composed of single campanulate flowers.
- *Length*.—Average range 20 cm to 30 cm.
- *Diameter*.—Average 5 cm.
- *Flowers per inflorescence*.—Average range 30 to 50.
- *Quantity per plant*.—40 to 50.
- *Flower attitude*.—Outward. Topmost flowers upward and outward.

Individual flower size:

- *Diameter*.—Approximately 2.4 cm.
- *Depth*.—Average 8 to 10 mm.

Peduncle:

- *Length*.—Average 10 to 16 cm.
- *Diameter*.—Approximately 3 mm.
- *Color*.—Near RHS Yellow-Green 146A with a very strong overall flush near Greyed-Purple N187B.
- *Texture*.—Glabrous, ridged.

Pedicel:

- *Length*.—Approximately 1.3 cm.
- *Diameter*.—Approximately 1 mm.
- *Color*.—Near RHS Green 138B.
- *Texture*.—Glabrous.

Corolla:

- *Petal arrangement*.—Fused corolla.
- *Shape*.—Campanulate, lobes approximately 1 cm deep, tube about 3 to 4 mm deep.
- *Petal margin*.—Entire.
- *Petal apex*.—Acute.
- *Petal quantity*.—5.
- *Petal shape*.—Lanceolate.
- *Texture*.—Glabrous, all surfaces.
- *Color*.—Petals: When opening: Inner surface: Near RHS Violet N88A. Outer surface: Near RHS Violet-Blue 90B. Fully opened: Inner surface: Near RHS Violet 88B, central vein faintly Violet-Blue N89B. Outer surface: Near RHS Violet-Blue 90C, with faint veins Violet N88A.

Throat:

- *Color*.—Near RHS White N155C.
- *Size*.—About 5 mm.

Tube:

- *Length*.—About 2 to 3 mm.
- *Diameter*.—About 3 to 4 mm.
- *Color*.—Exterior: Near RHS Violet-Blue 91D. Interior: Near RHS Violet 85D.

Bud:

*Shape*.—Ovate.

*Length*.—Approximately 7 mm.

*Width*.—Approximately 3 mm.

*Color*.—Near RHS Violet 85B striped Violet-Blue 90C.

Sepals:

*Quantity*.—5.

*Length*.—Approximately 7 mm.

*Width*.—Approximately 3 mm at base, 1 mm at apex.

*Shape*.—Narrow deltoid.

*Color*.—Interior Surface: Near RHS Green 138A, apex near Violet 86A. Exterior Surface: Near RHS Green 138A, apex near Violet 86B.

*Texture*.—Pubescent.

Fragrance: Very faintly musty.

Persistence: Flower semi-persistent. Petals dehiscence when completely dry.

REPRODUCTIVE ORGANS

Stamens:

*Number per flower*.—5.

*Filament length*.—3 mm.

*Filament color*.—Near RHS White 155C.

Anthers:

*Shape*.—Linear.

*Length*.—1 mm.

*Color*.—Near RHS White 155C.

Pollen: None.

Pistil:

*Quantity per flower*.—1.

*Length*.—Approximately 12 mm.

*Style*.—Length: Approximately 6 mm. Color: Near RHS White 155D.

*Stigma*.—Shape: 3-parted. Length: Approximately 1.5 cm. Color: Near RHS Violet 86D. Ovary Color: Near RHS Green 137D.

OTHER CHARACTERISTICS

Seeds and fruits: None.

Disease/pest resistance: Neither resistance nor susceptibility to common diseases and pests of *Campanula* has been observed.

Temperature tolerance: Can tolerate temperatures between −8° C. and 28° C.

What is claimed is:

1. A new and distinct cultivar of *Campanula* plant named 'Purple Fountain' as herein illustrated and described.

* * * * *